(12) United States Patent
Deimling

(10) Patent No.: US 8,154,288 B2
(45) Date of Patent: Apr. 10, 2012

(54) METHOD, PROCESSOR, AND MAGNETIC RESONANCE APPARATUS FOR SELECTIVE PRESENTATION OF LUNG MOVEMENT

(75) Inventor: Michael Deimling, Moehrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 378 days.

(21) Appl. No.: 12/570,156

(22) Filed: Sep. 30, 2009

(65) Prior Publication Data
US 2010/0090696 A1    Apr. 15, 2010

(30) Foreign Application Priority Data
Sep. 30, 2008    (DE) .................. 10 2008 049 709

(51) Int. Cl.
*G01V 3/00* (2006.01)
(52) U.S. Cl. ...................... 324/309; 324/307
(58) Field of Classification Search .......... 324/300–322; 600/407–445
See application file for complete search history.

(56) References Cited

U.S. PATENT DOCUMENTS

| | | | | |
|---|---|---|---|---|
| 5,755,725 | A * | 5/1998 | Druais ........................... | 606/130 |
| 6,962,587 | B2 * | 11/2005 | Johnson et al. ................. | 606/41 |
| 7,344,533 | B2 * | 3/2008 | Pearson et al. .................. | 606/41 |
| 2005/0033157 | A1 * | 2/2005 | Klein et al. .................... | 600/411 |
| 2008/0281314 | A1 * | 11/2008 | Johnson et al. ................. | 606/34 |
| 2008/0287944 | A1 * | 11/2008 | Pearson et al. .................. | 606/41 |

FOREIGN PATENT DOCUMENTS
DE    10 2005 010 093 A1    9/2006

OTHER PUBLICATIONS

"Brain Mapping: New Wave Optical Imaging," Mrsic-Flogel et al., Current Biology, vol. 13 (2003) pp. R778-R780.
"Reduction of Physiological Fluctuations in fMRI Using Digital Filters," Biswal et al., Magnetic Resonance in Medicine, vol. 35 (1996) pp. 107-113.
"Measuring Quantitative Regional Lung Ventilation by Alveolar Ventilation Imaging (AVI)—Phantom Data and results of a Feasibility Study in 50 patients," Topf et al., ISMRM 2004, May 2004.
Temporal Dynamics of Blood flow Effects in Half-Fourier Fast Spin Echo $^1$H Magnetic Resonance Imaging of the Human Lungs, Knight-Scott et al., Journal of Magnetic Resonance Imaging, vol. 14 pp. 411-418 (2001).

(Continued)

*Primary Examiner* — Brij Shrivastav
(74) *Attorney, Agent, or Firm* — Schiff Hardin LLP

(57) ABSTRACT

In a method for selective presentation of a movement of the lung, magnetic resonance images (MR images) of the lung are acquired in a temporal progression, i.e. MR images of the lung are acquired over multiple breathing cycles. The acquired MR images are registered with regard to a reference position and the signal curve over time is determined in the acquired MR images. The frequency spectrum of the determined signal curves is then determined, such as by a Fourier transformation. A specific frequency spectrum is filtered with a frequency band filter, wherein the frequency range of the frequency band filter is adapted to the movement to be shown. The filtered frequency spectrum is transformed back into a filtered signal curve of the MR images, and the magnetic resonance images obtained via this back-transformation are displayed in the temporal progression with the filtered signal curve. A computer readable medium, an image processing unit and a magnetic resonance apparatus implement such a method.

11 Claims, 2 Drawing Sheets

OTHER PUBLICATIONS

"Influence of Oxygen Flow Rate on Signal and $T_1$ Changes in Oxygen-Enhanced Ventilation Imaging," Mai et al., of Magnetic Resonance Imaging, vol. 16, (2002) pp. 37-31.

"MRI Estimation of Dynamic Regional Lung Ventilation, Derived from Pulmonary Density Changes During Respiration," Marcus et al., Proc. Intl. Soc. Magn. Reson. Med. vol. 15, (2007).

"True FISP Imaging of Lunch Parenchyma at 0.2 Tesla," Deimling, vol. 11 No. 2202 (2000).

"Power Spectrum Analysis of Functionally-Weighted MR Data: What's in the Noise?" Weisskoff et al., In: Proc. of the Society for Magnetic Resonance, vol. 1, (1993) p. 7.

* cited by examiner

METHOD, PROCESSOR, AND MAGNETIC RESONANCE APPARATUS FOR SELECTIVE PRESENTATION OF LUNG MOVEMENT

BACKGROUND OF THE INVENTION

1. Field of the Invention

The invention concerns a method for selective presentation of a movement of the lung, as well as a computer-readable medium, an image processing unit and a magnetic resonance apparatus that implements such a method.

2. Description of the Prior Art

The magnetic resonance technique (in the following "MR" stands for "magnetic resonance") is a known technique with which images of the inside of an examination subject can be generated. Described simply, the examination subject is positioned in a strong, static, homogeneous basic magnetic field (field strengths from 0.2 Tesla to 7 Tesla or more) inside an MR apparatus so that the nuclear spins of the examination subject orient along the basic magnetic field. To excite nuclear magnetic resonances, sequences of radio-frequency excitation pulses are radiated into the examination subject, the excited nuclear magnetic resonance signals are detected, and MR images are reconstructed based thereon. The MR technique is particularly suitable for imaging of soft tissues since a particularly good contrast can be achieved.

The imaging of the lungs by means of MR has also been promoted for years, primarily in order to draw conclusions about the functioning of the lungs. However, various difficulties exist in this context. The proton densities in the region of the lung filled with air and also the proton densities of the lung parenchyma itself are very low, which leads to a poor signal-to-noise ratio (SNR). Moreover, local field changes that arise due to susceptibility changes make the MR imaging more difficult. Furthermore, the region of the lung is subject to movements due to both breathing and the heart beat of the patient to be examined, which movements lead to movement artifacts in MR images. In particular the breathing movement changes not only the position of the tissue to be acquired but also the total volume of the lung. An additional effect that hinders the qualitative evaluation of lung data is the strong, varying blood flow in the lung within a cardiac cycle.

In order to confront these difficulties, MR images of the lungs are conducted with enhancement using contrast agent such as helium or oxygen, for example. One example of oxygen-enhanced imaging is, described in Vu M. Mai et al., "Influence of Oxygen Flow Rate on Signal and T1 Changes in Oxygen-Enhanced Ventilation Imaging" in the Journal of Magnetic Resonance Imaging 16: 37-41, 2002.

Due to the short acquisition times for MR images that are able to be currently achieved, it is also possible to acquire exposures of the lungs by means of MR tomography without severe movement artifacts. Triggering of the sequence workflow with the external movement (the breathing or the heart bear), however must often ensue, or the breath must be held for the duration of the acquisition. One example of a heart beat-triggered imaging is described in Knight-Scott J. et al. "Temporal Dynamics of Blood Flow Effects in Half-Fourier Fast Spin Echo 1H Magnetic Resonance Imaging of the Human Lung" in the Journal of Magnetic Resonance Imaging 14: 411-418, 2001.

For basic field strengths of more than 0.7 T, the T2* relaxation time is very short due to susceptibility (M. Deimling in Proc. Int. Soc. Magn. Reson. Med. 8 (2000), No. 2202). Therefore spin echo-based sequences (for example single shot HASTE) are used to show the lung parenchyma since spin echo sequences suppress the influence of susceptibility changes (see again Vu M. Mai et al. in the Journal of Magnetic Resonance Imaging 16: 37-41, 2002).

In recent tomography systems, very short echo times can be achieved so that gradient echo sequences can be applied even at basic field strengths of up to 1.5 T, for example (see for example Marcus, J. T. et al. in Proc. Int. Soc. Mag. Reson. Med. (2007), No. 2777).

In evaluations of image series of the lung, for example in a temporal progression, the problem as described above occurs of the size of the lung varying due to inhaling and exhaling. This leads to a displacement of corresponding regions in the different MR images since the lung occupies different positions in different MR images. Methods are known that can fix different lung image sizes in the breathing cycle to a reference size, and with which a registration of the individual images to one another is made possible (H. G. Topf et al. in Proc. Int. Soc. Magn. Reson. Med 11 (2004) No. 671). It has therefore become possible to analyze signal changes due to density changes as a function of time. The signal-emitting volume varies due to inhaling and exhaling, such that the breathing movement leads to the signal changes. For example, ventilation defects in the lung can be made visible by the depiction of the signal changes. However, one problem that occurs is that the signal changes depend not only on the changing parenchyma density but also on the signal of the blood that propagates in and out of the bronchial vessels with the cardiac rhythm. This blood signal interferes with the analysis of the lung signal change.

A method to depict respiration patterns by a separation of the signal portions of the blood from signal portions of the lung parenchyma in a magnetic resonance image is known from DE 10 2005 010 093 A1 and includes the following steps. Magnetic resonance images of the lung are acquired in a temporal procession, the signal curve in the magnetic resonance images over time is calculated followed by a Fourier transformation of the temporal signal curve, extraction of the Fourier spectrum belonging to the lung parenchyma, and presentation of information in the magnetic resonance image that is contained in the Fourier spectrum. The acquired information from the spectrum is thereby statically superimposed on an anatomical map of the lung.

Another example of an evaluation of spectra in MR images is described by Weisskoff, R. M., Baker, J., Belliveau, J., Davis, T. L., Kwong, K. K., Cohen, M. S., & Rosen, B. R. in "Power spectrum analysis of functionally-weighted MR data: What's in the noise?", Proceedings of the Society for Magnetic Resonance, 1, 7 (1993).

SUMMARY OF THE INVENTION

An object of the present invention is to improve lung imaging such that dynamic processes can be selectively shown.

The method according to the invention for selective presentation of a movement of the lung includes the following steps. First, magnetic resonance images of the lung are acquired in a temporal progression, meaning that magnetic resonance images (MR images) of the lung are acquired over multiple breathing cycles. The acquired MR images are registered with regard to a reference position and the signal curve over time is determined in the acquired MR images. This advantageously occurs on a pixel-by-pixel basis in order to be able to fully utilize the resolution of the MR images. The frequency spectrum of the determined signal curves is then determined, for example by means of a Fourier transformation. A specific frequency spectrum is filtered with a frequency band filter with the frequency range of the frequency band filter being adapted to the movement to be shown. The filtered frequency spectrum is transformed back into a filtered signal curve of the MR images, and the magnetic resonance images obtained through this back-transformation are displayed in the temporal progression with the filtered signal curve.

With the method according to the invention, it is possible to selectively show the dynamic of lung parenchyma or blood of a perfused tissue without contrast agent, thus without external agents such as oxygen or helium, for example. It is thus not necessary for the patient to hold his or her breath, instead, the patient can breath normally.

It is furthermore an object of the present invention to provide a computer-readable medium, an image processing unit and a magnetic resonance apparatus that enable dynamic processes to be selectively shown in temporal progression in a series of MR images, by implementing or executing the above-described method and all embodiments thereof.

DESCRIPTION OF THE PREFERRED EMBODIMENTS

Figure 1:
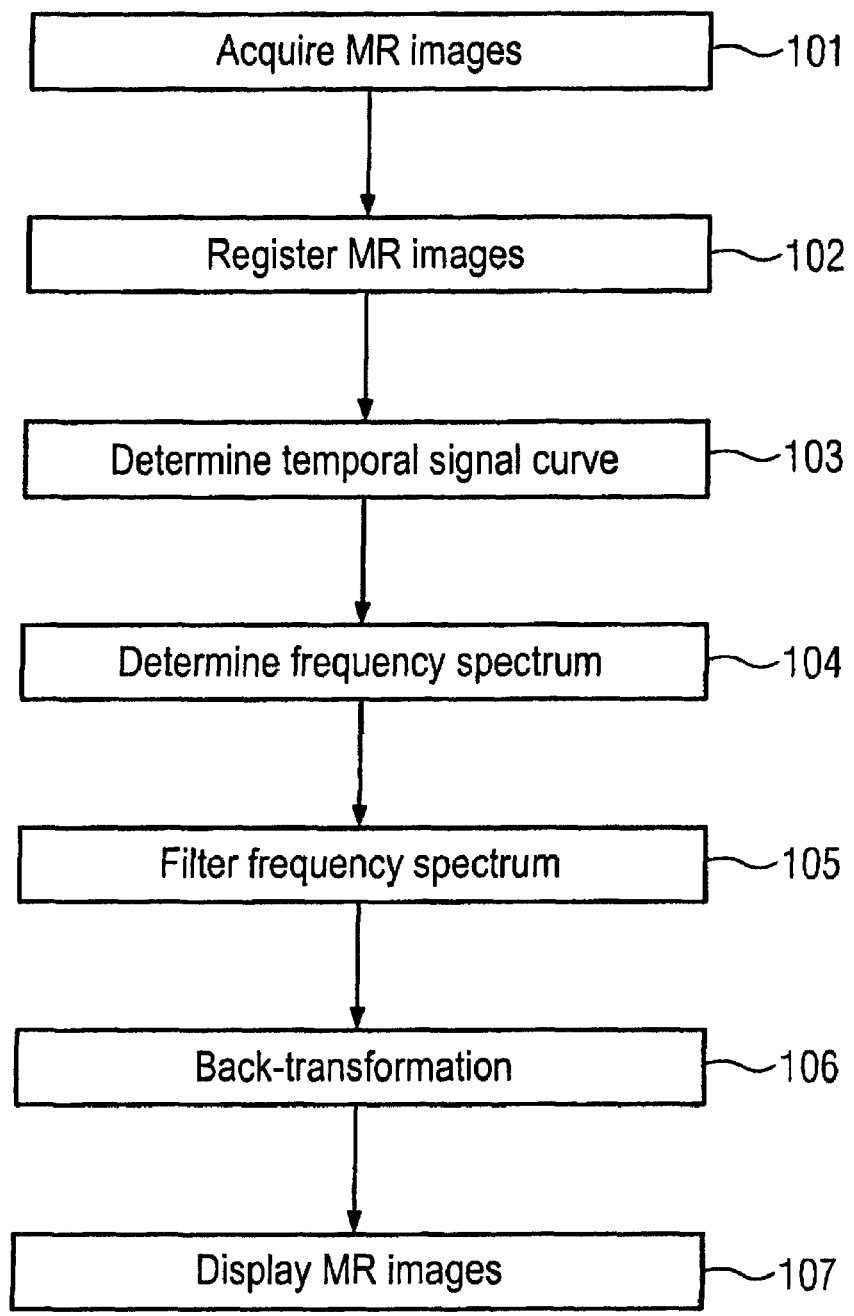
FIG. 1 is a flow chart of an exemplary embodiment of a method for selection presentation of a movement of the lung in accordance with the invention.

FIG. 1 shows a flow chart of an exemplary method for selective presentation of a movement of the lung. Multiple MR images of the lung are thereby initially acquired in a temporal progression in Step 101. for example, a series of N=100 MR images or more (however at least N=20 MR images) of the lung is acquired in a temporal progression of a movement of the lung.

The selection of the measurement sequence used in the acquisition of these MR images typically depends on the selection of the magnetic resonance apparatus that is used, in particular here on the basic field strength. By the application of very short echo times TE, gradient echo sequences and even SSFP (Steady State Free Precession) sequences can also be advantageously used, wherein the measurement time per MR image should likewise lie in the range from approximately 0.1-0.5 sec, advantageously 0.3 sec.

In a further Step 102, the acquired images are registered. This occurs as described in the previously cited publication by H. G. Topf et al., for example, via an elastic pixel transformation of the individual images that relate to a reference quantity. The same locations in the individual MR images can therefore be assumed to be the same locations in the acquired examination subject (here the lung).

In a further Step 103, the signal curve 21 in the MR images is determined over time. For this a curve of an intensity of the MR signal over time in the MR images is advantageously determined per pixel. It can thereby already be sufficient to determine the signal curves of the individual pixels of the MR images only in one region of interest (determined by means of a segmentation method, for example) in each MR image in order to further reduce cost and time. In particular the imaged lung and/or the bronchial vessels are considered as a region of interest. Alternatively, the signal curve can also be averaged across groups of pixels of the MR images, wherein this leads to losses in resolution.

Figure 2:
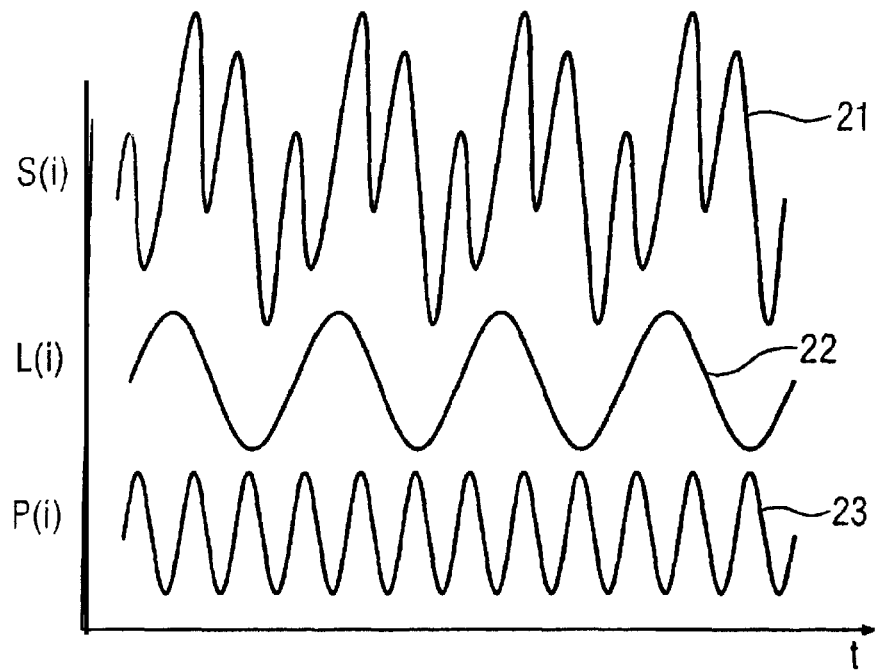
FIG. 2 shows an exemplary signal curve.

FIG. 2 shows an example of such a signal curve 21 of a pixel i over time.

The determined signal curve 21 could contain, for example, sinusoidal oscillations that result due to period movements in the acquired subject (here the lung). Typical periodic movements are in particular movements due to blood circulation and due to the density change of the lung parenchyma that are caused by the breathing of the patient.

In order to be able to separate the information with regard to the different movements that is contained in the MR images, in a further Step 104 the frequency spectrum of the signal curve 21 is determined. This Step can advantageously be implemented by means of a Fourier analysis. However, other prevalent methods can also be applied, for example a decomposition in the sine or $\sin^\lambda(t)$ functions. Individual frequency portions of the temporal signal curve 21 can be detected as maxima in the frequency spectrum.

One example of such a frequency spectrum is provided in FIG. 3, described in detail below.

In a further Step 105, a frequency band filter 35 whose frequency range is adapted to the movement to be shown is applied to an acquired frequency spectrum. The frequency portion of the movement to be shown can thus be filtered out of the total frequency spectrum. The movement to be shown can thereby be movement caused by a breathing or movement caused by cardiac activity, for example.

In a further Step 106, the filtered frequency spectrum 34 is transformed back again into a (now filtered) signal curve. The inverse method relative to the method applied in Step 104 is thereby advantageously applied to determine the frequency spectrum. If the frequency range of the frequency band filter from Step 105 was adapted to the breathing movement, the filtered signal curve received via the back-transformation corresponds to a signal change due to the breathing movement. If the frequency range of the frequency band filter from Step 105 was adapted to the cardiac activity, the filtered signal curve received via the back-transformation corresponds to a signal change due to the cardiac activity. An exemplary signal curve 22 in a pixel i of the MR images for a signal change due to a breathing movement and an exemplary signal curve 23 in a pixel i of the MR images for a signal change due to cardiac activity are shown in FIG. 2.

In a last Step 107, the acquired filtered signal curves are displayed again as MR images with the filtered signal curve in a temporal progression. A series of MR images in a temporal progression in which the dynamic of the movement filtered out by the frequency band filters and the anatomy of the lung are simultaneously recognizable is obtained in this way in a simple manner. A superimposition of the information obtained from the frequency spectrum with an anatomical image can thus be omitted. Moreover, the presentation of the movement in the lung is not static, but rather is provided dynamically over the temporal progression, which enables a more precise analysis of the function of the lung.

The frequency spectrum determined in Step 104 can also be filtered in succession with a first frequency band filter (that, for example, is adapted to a breathing movement) and with a second frequency band filter (that, for example, is adapted to a movement caused by the cardiac activity) so that two respective filtered signal curves are generated. The dynamic of the different movements independent of one another can thus be displayed in the respective Steps 107. The individual depictions are respectively free of influences of other movements that are not to be shown and two which the corresponding frequency band filters were not adapted.

Before the back-transformation in Step 106, the frequency-sorted MR images associated with the selected frequency range in Step 105 can be assembled into a resulting image at the center frequency of the frequency band filter by taking the sum of squares of the MR images weighted by the filter curve, for example.

Figure 3:
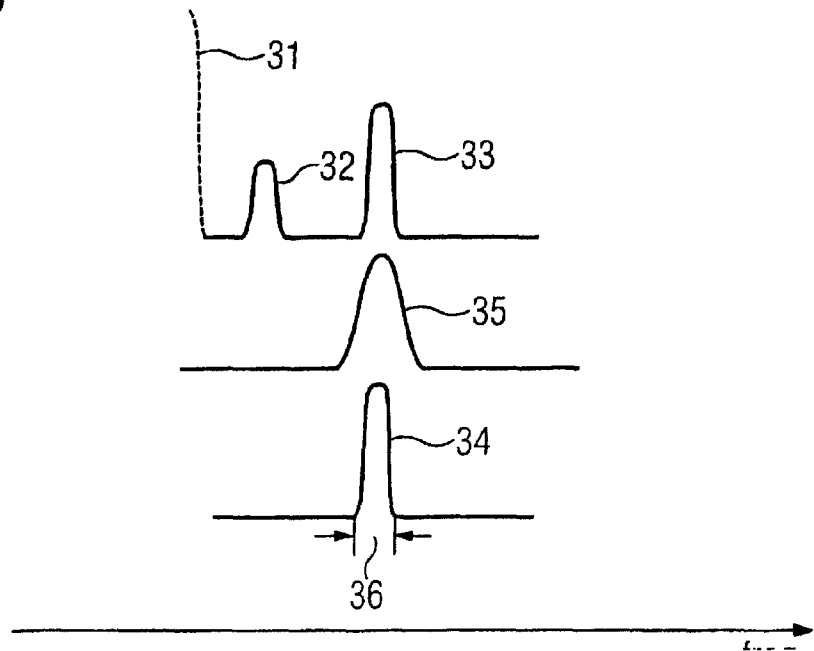
FIG. 3 shows frequency spectra that can occur during the movement.

A typical frequency spectrum with maxima 31, 32 and 33 is shown at the top in FIG. 3. The maximum 31, which corresponds to the constant component of the spectrum given a frequency v=0. An additional maximum 33 that corresponds to the frequency portion of the blood in the signal curve 21 that is caused by the cardiac frequency lies at a higher frequency than a maximum 32 that corresponds to the frequency portion of the change of the density of the lung parenchyma in the signal curve 21 that results due to the (in comparison to the cardiac frequency) low-frequency breathing. As indicated by the dotted depiction of the maximum 31, the constant component can advantageously be subtracted from the determined frequency spectrum.

A frequency band filter 35 can advantageously be a Gaussian function with a frequency range 36 at a frequency portion adapted to a movement to be shown. The frequency portion adapted to the movement is determined from the frequency spectrum as a frequency of the maximum of the movement to be shown. The frequency range of the frequency band filter can also advantageously be determined by the defined frequency portions in the frequency spectrum of the determined signal curve. For example, this advantageously occurs via a determination of the width of the appertaining maximum in the frequency spectrum. Alternatively, a certain tolerance range can also be provided as a frequency range. The frequency range of the frequency band filter includes the frequency portion of the signal curve that corresponds to the movement to be shown.

It is also possible to determine the frequency portion that the frequency band filter should filter out of the frequency spectrum by an external measurement of the movement to be shown, for example via pulse measurement or breathing movement measurement, for instance by a breathing belt. However, this is complicated and unnecessary.

In FIG. 3 the frequency band filter 35 is represented as a Gaussian function over the maximum that corresponds to the frequency portion of a movement caused by the cardiac activity. The spectrum 34 filtered with this frequency band filter 35 thus contains only one maximum 34 that corresponds to the maximum 33 that corresponds to the movement caused by the cardiac activity.

Analogously, a frequency spectrum filtered with a frequency band filter that is across the frequency portion corresponding to the breathing movement still has only one maximum that corresponds to the breathing movement. This is not explicitly shown again for reasons of clarity.

As already mentioned above, the signal curve 21 of the MR images is advantageously determined on a pixel-by-pixel basis, and the analysis of the signal curve 21, filtering and back-transformation in a filtered signal curve 22 or, respectively, 23 is likewise conducted per pixel. In this way MR images with filtered signal curve are obtained that have the same resolution as the originally acquired MR images but that selectively show either the influence of the breathing movement or the influence of the movement in the lung caused by the cardiac activity.

Although modifications and changes may be suggested by those skilled in the art, it is the intention of the inventor to embody within the patent warranted hereon all changes and modifications as reasonably and properly come within the scope of his or her contribution to the art.

I claim as my invention:

1. A method for selective presentation of a movement of the lung, comprising the steps of:
    with a magnetic resonance data acquisition unit, acquiring a series of magnetic resonance images of the lung in a temporal progression;
    in a non-transitory computer, registering the magnetic resonance images relative to a reference position;
    in said computer, determining signal curve over time in the acquired MR images;
    in said computer, determining a frequency spectrum of the signal curve;
    filtering the frequency spectrum with a frequency band filter having a frequency range adapted to a movement to be shown;
    in said computer, transforming the filtered frequency spectrum back into a filtered signal curve of the magnetic resonance images; and
    from the computer, displaying the magnetic resonance images obtained by the back-transformation in the temporal progression with the filtered signal curve.

2. Method according to claim 1, comprising setting the frequency range of the frequency band filter dependent on frequency components in the specific signal curve.

3. Method according to claim 2, comprising identifying the frequency components of the signal curve by a Fourier analysis of the signal curve.

4. Method according to claim 2 comprising setting the frequency range of the frequency band filter to include a frequency component of the signal curve that corresponds to the movement to be shown.

5. Method according to claim 4, comprising employing in said frequency band filter, a Gaussian function of the frequency component of the signal curve that corresponds to the movement to be shown.

6. Method according to claim 1 comprising in said computer, determining the signal curve over time on a pixel-by-pixel basis in the magnetic resonance images.

7. Method according to claim 1 wherein the movement to be shown is a breathing movement.

8. Method according to claim 1 wherein the movement to be shown is a movement caused by a cardiac activity.

9. A non-transitory computer processor for selective presentation of a movement of the lung represented in a series of magnetic resonance images of the lung acquired in a temporal progression with a magnetic resonance data acquisition unit, said processor being configured to:
    register the magnetic resonance images relative to a reference position;
    determine signal curve over time in the acquired MR images;
    determine a frequency spectrum of the signal curve;
    filter the frequency spectrum with a frequency band filter having a frequency range adapted to a movement to be shown;
    transform the filtered frequency spectrum back into a filtered signal curve of the magnetic resonance images; and
    cause the magnetic resonance images obtained by the back-transformation to be displayed at a display in the temporal progression with the filtered signal curve.

10. A magnetic resonance apparatus for selective presentation of a movement of the lung, comprising:
- a magnetic resonance data acquisition unit that acquires a series of magnetic resonance images of the lung in a temporal progression;
- a non-transitory computer configured to register the magnetic resonance images relative to a reference position;
- said computer being configured to determine signal curve over time in the acquired MR images;
- said computer being configured to determine a frequency spectrum of the signal curve;
- a frequency band filter that filters the frequency spectrum, said frequency band filter having a frequency range adapted to a movement to be shown;
- a computer being configured to transform the filtered frequency spectrum back into a filtered signal curve of the magnetic resonance images; and
- a display at which, from the computer, the magnetic resonance images obtained by the back-transformation are displayed in the temporal progression with the filtered signal curve.

11. A non-transitory computer-readable medium encoded with programming instructions for selective presentation of a movement of the lung, said medium being loaded into a non-transitory computer system of a magnetic resonance imaging apparatus, and said programming instructions causing said computer system to:
- operate a magnetic resonance data acquisition unit of the apparatus to, acquire a series of magnetic resonance images of the lung in a temporal progression;
- register the magnetic resonance images relative to a reference position;
- determine signal curve over time in the acquired MR images;
- determine a frequency spectrum of the signal curve;
- filter the frequency spectrum with a frequency band filter having a frequency range adapted to a movement to be shown;
- transform the filtered frequency spectrum back into a filtered signal curve of the magnetic resonance images; and
- display the magnetic resonance images obtained by the back-transformation in the temporal progression with the filtered signal curve.

* * * * *